United States Patent [19]

Mundt

[11] Patent Number: 5,100,799
[45] Date of Patent: Mar. 31, 1992

[54] METHOD FOR RELEASING CELL CULTURES FROM MICROCARRIERS

[75] Inventor: Wolfgang Mundt, Vienna, Austria

[73] Assignee: Immuno Aktiengesellschaft, Fed. Rep. of Germany

[21] Appl. No.: 274,430

[22] Filed: Nov. 21, 1988

[30] Foreign Application Priority Data

Nov. 23, 1987 [DE] Fed. Rep. of Germany ....... 3739649

[51] Int. Cl.$^5$ ............................................. C12N 5/00
[52] U.S. Cl. .............................. 435/240.24; 435/174; 435/240.23; 435/286
[58] Field of Search .................. 435/174, 240.24, 261, 435/286, 240.2, 240.23, 284

[56] References Cited

U.S. PATENT DOCUMENTS

| | | | |
|---|---|---|---|
| 4,201,845 | 5/1980 | Feder et al. | 435/285 |
| 4,237,218 | 12/1980 | Monthony et al. | 435/2 |
| 4,545,909 | 10/1985 | Atkinson et al. | 210/618 |

FOREIGN PATENT DOCUMENTS 0259179 12/1985 Japan.
WO86/01531 3/1986 PCT Int'l Appl..

*Primary Examiner*—David L. Lacey
*Assistant Examiner*—William H. Beisner
*Attorney, Agent, or Firm*—Sterne, Kessler, Goldstein & Fox

[57] ABSTRACT

This invention relates to a method for releasing cell cultures from microcarriers in which a trypsin solution is directed through a container with the microcarriers therein in a flow-through process. The released cells are immediately withdrawn from the carrier, with the trypsin solution being inactivated and/or removed after leaving the container.

6 Claims, 1 Drawing Sheet

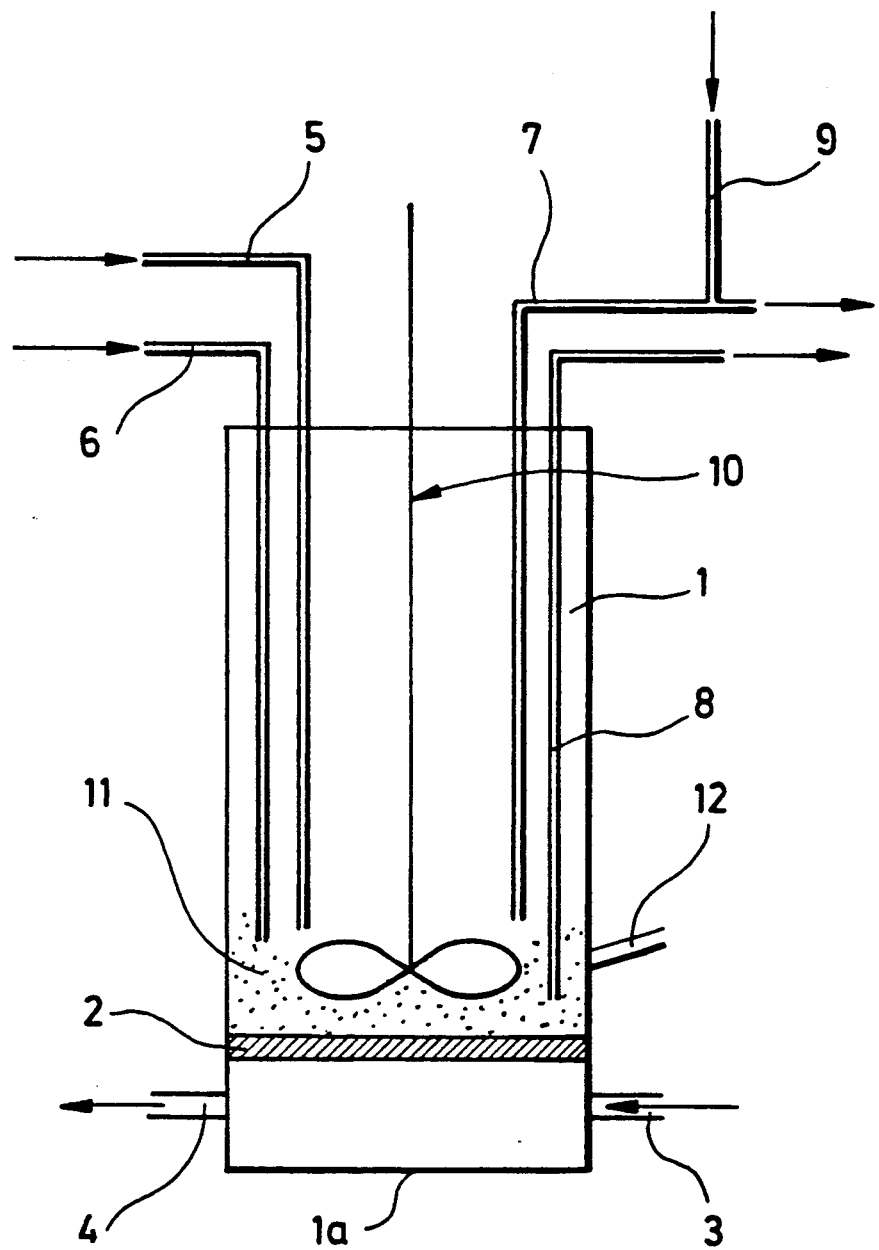

METHOD FOR RELEASING CELL CULTURES FROM MICROCARRIERS

FIELD OF THE INVENTION

The invention relates to a method for releasing cell cultures from microcarriers using a trypsin solution.

The method serves the production of cell cultures by propagating them on microcarriers. For obtaining greater amounts of cell cultures, the cultures have to be released from the microcarriers and to be resettled on unoccupied microcarriers. These operations have hitherto been carried out in a batch-wise process (WO 86/01531). Trypsin is added to a container containing populated microcarriers for causing the cells to be released therefrom. The removal of the cells, i.e. a cell suspension containing the cells, from the container is deferred until substantially all of the cells have been released from the microcarriers. A high percentage of the cells is released rather quickly and therefore remains in the trypsin solution for a long time. This results in the disadvantage that the action of the trypsin exerts an adverse influence on these cells. It is particularly their growth and their resettlement capability on new microcarriers that is adversely affected. This becomes particularly critical in the case of greater volumes in which the cultures are inhomogeneous and widely varying release rates have to be reckoned with.

SUMMARY OF THE INVENTION

It is an object of the present invention to provide a method of the type defined above in which the time during which the trypsin acts on the released cells is reduced to a minimum.

This object is attained according to the invention by a method for releasing cell cultures from microcarriers, wherein a trypsin solution is introduced into a container containing occupied carriers, and the released cells are removed from the container, characterized in that said trypsin solution is directed through said carrier and thus through said microcarriers in a flow-through process, and released cells are thus immediately entrained out of the container, the trypsin solution being inactivated and/or removed after leaving the container.

In this method, released cells are removed from the container at a rate corresponding to the flow-through speed of the trypsin solution and subsequently removed from the adverse action of the solution. The flow-through of the trypsin solution may be continued as long as required for separating even the last cell cultures from the microcarriers. The time during which the trypsin acts on released cells is of substantially the same short duration during each phase.

The flow-through of the trypsin solution which is pumped through the container from below in an upward direction offers the advantage that released cells are prevented from settling in the bottom region of the container and are instead removed from the region of the microcarriers in the direction of flow.

The flow-through rate of the trypsin solution is selected so that microcarriers are kept in a floating state, is directed to an advantageous embodiment of the method in which the flowing solution sweeps the microcarriers on all sides to thereby accelerate the release process.

In another embodiment, the trypsin solution is supplied from below through a permeable insert to the space of the container containing said microcarriers offers the advantage that the trypsin solution impinges on the microcarriers and their cell cultures in a uniform distribution and with a homogeneous flow speed distribution.

The released cells are advantageously transferred to another container containing bare microcarriers permitting their further growth to start immediately.

The invention also provides an apparatus for performing the method of a construction for the procreation of cell cultures, comprising a container for containing microcarriers, characterized by a feed pipe (3) for a trypsin solution and a discharge pipe (7) for the removal of a suspension containing release cells permitting the through-flow of the trypsin solution.

There are advantageous developments of the apparatus permitting the advantageous embodiments of the method described to be performed. The apparatus is also characterized in that container (1) contains a permeable insert (2) at a spaced location from its bottom (1a), the feed pipe (3) for the trypsin solution opening into the container below said insert (2). The apparatus is further characterized in that the discharge pipe (7) begins in the container (1) above said permeable insert (2). The apparatus is also characterized in that outside of the container (1) the discharge pipe (7) communicates with a feed pipe (9) for a medium for inactivating and/or removing trypsin.

This advantageous embodiment permits the passage of a washing buffer liquid through the container from top to bottom prior to the introduction of the trypsin solution.

The apparatus is further characterized in that a feed port (5) for a washing buffer liquid opens into an upper container portion, a closeable drain opening (4) being provided in the bottom region below said permeable insert (2).

The apparatus is further characterized in that a drain pipe (8) for the removal of microcarriers (11) from said container (1) extends from a location closely above said insert (2) upwards out of said container (1).

The preparation of the used container and the used microcarriers for renewed use is advantageously facilitated by this embodiment.

BRIEF DESCRIPTION OF THE DRAWINGS

The method according to the invention shall now be explained with reference to a diagrammatically depicted apparatus shown in the single figure of the drawing.

DESCRIPTION OF THE PREFERRED EMBODIMENT(S)

In a closed container 1, a permeable insert 2, for instance a sieve or a porous plate, is disposed at a distance above its bottom 1a. Below insert 2 a feed pipe 3 opens into container 1 for the supply of a trypsin solution. Also in a wall portion of container 1 between bottom 1a and insert 2 there is a closeable drain opening 4 for draining a washing buffer liquid. Opening into container 1 above permeable insert 2 are a feed port 5 for a washing buffer liquid and a feed port 6 for a cell procreation medium. Extending into container 1 from above are a discharge pipe 7 for removing a suspension containing released cells, and a drain pipe 8, the inlet opening of the latter being disposed closely above insert 2. Outside of container 1 discharge pipe 7 communicates with a feed pipe 9. Discharge pipe 7 also contains a suction pump not shown here.

Also extending into container 1 from above is a stirrer element 10 mounted outside of container 1 and adapted to be actuated in a manner not shown.

Disposed above permeable insert 2 is a layer of microcarriers of any suitable height as indicated by dots. Prior to the beginning of the method to be described, these microcarriers 11 have had cell cultures settled thereon, which have grown until microcarriers 11 are fully occupied thereby. This state can be ascertained by drawing a sample at a sampling port 12 above insert 2. The method is started by passing a washing buffer solution through the container's contents, this solution entering through feed port 5 and flowing off through the simultaneously opened drain opening 4. After drain opening 4 has then been closed, a trypsin solution is pumped into container 1 through feed pipe 3. The solution is distributed by passing through permeable insert 2 and is directed onto microcarriers 11 with a light and uniform flow pressure, so that the microcarriers are maintained in a floating state. The action of the trypsin causes the cell cultures to be released from the microcarriers. The trypsin solution is withdrawn from the container in a flow-through process by means of a suction pump connected to discharge pipe 7. In this manner the released cells are immediately entrained and removed from the container. At the same time a medium for deactivating and/or separating the trypsin from the solution is introduced into discharge pipe 7 through feed pipe 9. In this manner the withdrawn cells are relieved of further action of the trypsin thereon. They may then be transferred directly to another container containing unoccupied microcarriers.

The through-flow of the trypsin solution is maintained until substantially all cell cultures have been released and withdrawn from the container.

At this stage the flow rate of the trypsin solution is selected so that the microcarriers 11 are kept in a floating state to permit the trypsin solution to act thereon from all sides, and released cells are rapidly carried away.

After all of the cell cultures have been thus removed, the substantially bare microcarriers are removed from the container through drain pipe 8. They are subsequently prepared for renewed occupation, as is also container 1.

Stirrer element 10 may selectively be actuated for accelerating the mixing process of the microcarriers with the washing buffer solution if so desired.

I claim:

1. A method for releasing cells from microcarriers comprising introducing a trypsin solution into a container containing cells immobilized on cell culture microcarriers and directing said trypsin solution through said container, in the absence of mechanical agitation, in a continuous flow such that the cells are released from the microcarriers and said released cells and said trypsin solution are quickly removed from said container such that said trypsin solution is at least inactivated or separated from said released cells.

2. The method according to claim 1, wherein said trypsin solution is pumped through said container.

3. The method according to claim 2, wherein said trypsin solution is pumped in a direction and at a flow-through rate so that said microcarriers are maintained in a floating state.

4. The method according to any one of claims 1 to 3, wherein a permeable insert is positioned in said container to define a bottom space and an upper space containing said microcarriers and said trypsin solution is supplied from said bottom space to flow in an upward direction through said permeable insert to said upper space.

5. The method according to claim 1, wherein said released cells are transferred to a container containing unoccupied microcarriers.

6. The method according to claim 1, further comprising introducing a washing buffer liquid through said container in a continuous flow prior to the introduction of said trypsin solution.

* * * * *